United States Patent
McDaniel et al.

(10) Patent No.: US 6,368,662 B1
(45) Date of Patent: Apr. 9, 2002

(54) MOLECULAR LEVEL COATING OF METAL OXIDE PARTICLES

(75) Inventors: Patricia R. McDaniel, Hampton; Terry L. St. Clair, Poquoson, both of VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/495,575

(22) Filed: Feb. 1, 2000

Related U.S. Application Data

(62) Division of application No. 08/742,068, filed on Oct. 31, 1996, now Pat. No. 6,114,156.

(51) Int. Cl.$^7$ .............................. B05D 7/14; B05D 7/24; B05D 1/00
(52) U.S. Cl. ........................................ 427/216; 427/221
(58) Field of Search ............................. 427/212, 213.3, 427/213.31, 213.34, 220, 221, 214, 215

(56) References Cited

U.S. PATENT DOCUMENTS

| | | | | |
|---|---|---|---|---|
| 4,065,345 A | * | 12/1977 | Progar et al. | 159/309 |
| 4,937,317 A | * | 6/1990 | Pratt et al. | 528/353 |
| 5,536,846 A | * | 7/1996 | Dellacoletta et al. | 549/252 |
| 6,235,270 B1 | * | 6/2001 | Ishii et al. | 424/59 |

* cited by examiner

Primary Examiner—Shrive P. Beck
Assistant Examiner—Rebecca Blanton
(74) Attorney, Agent, or Firm—Robin W. Edwards

(57) ABSTRACT

Polymer encapsulated metal oxide particles are prepared by combining a polyamide acid in a polar aprotic solvent with a metal alkoxide solution. The polymer was imidized and the metal oxide formed simultaneously in a refluxing organic solvent. The resulting polymer-metal oxide is an intimately mixed commingled blend, possessing synergistic properties of both the polymer and preceramic metal oxide. The encapsulated metal oxide particles have multiple uses including, being useful in the production of skin lubricating creams, weather resistant paints, as a filler for paper, making ultraviolet light stable filled printing ink, being extruded into fibers or ribbons, and coatings for fibers used in the production of composite structural panels.

5 Claims, 3 Drawing Sheets

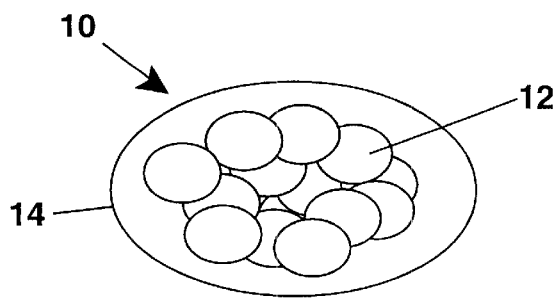
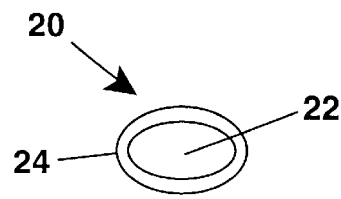
FIG 1
FIG 2
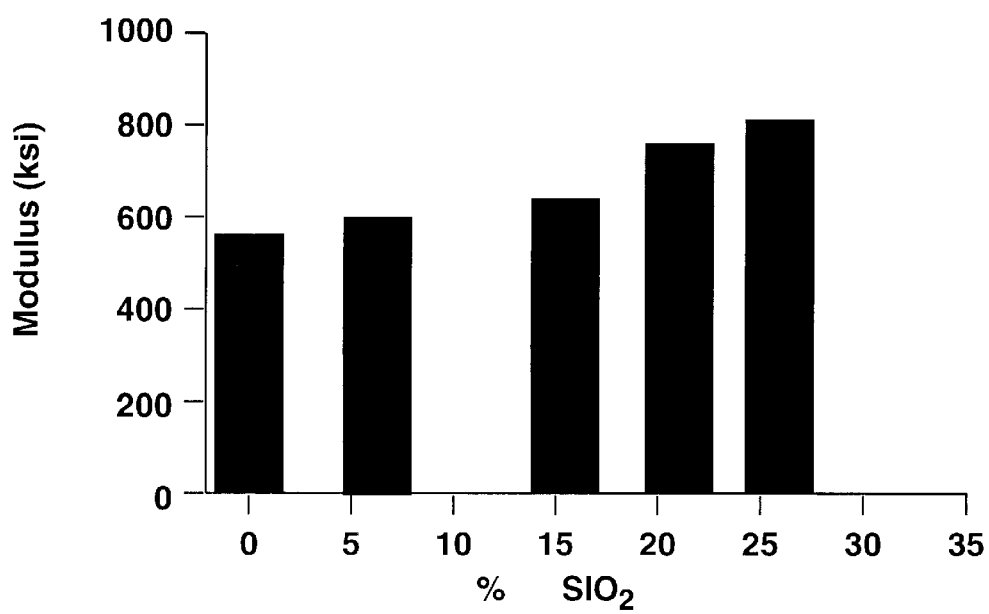
FIG 3

MOLECULAR LEVEL COATING OF METAL OXIDE PARTICLES

This application is a divisional patent application of, commonly owned patent application Ser. No. 08/742,068, filed Oct. 31, 1996 and now U.S. Pat. No. 6,114,156.

ORIGIN OF THE INVENTION

The invention described herein was made by an employee of the United States Government and a National Research Council Associate which may be used by or for the Government for governmental purposes without the payment of any royalties thereon or therefor.

FIELD OF THE INVENTION

This invention relates generally to the preparation of coatings, molding powders, fibers, films and matrix resins for composites. The invention relates specifically to the molecular level coating of metal oxide particles with polyimides and the product(s) obtained thereby.

BACKGROUND OF THE INVENTION

The development of advanced high performance polymers for aerospace applications has been, and remains, a particularly active area of research. High performance polyimides have found extensive use in the aerospace industry as adhesives, and more recently as matrix resins for composites, molding powders and films.

Improvements in high performance systems are motivated by the search for advanced materials with improved or unique properties. Previous research into polyimide modifications have involved the simplest and most inexpensive methods involving manipulation of the chemical composition of mainly linear polyimides. An alternative method of modification is by incorporation of a second component of differing chemical structure or composition.

Modifications utilizing the morphology of multiphase systems with phases of differing chemical structure allows for a remarkable balance of diverse properties. This is especially true when at least one phase is on the molecular scale, allowing for a balance of diverse properties. The production of organic-inorganic hybrid materials may take place through several different methods. One route is by direct mixing of low melt glasses with engineering thermoplastics, Beall and Quinn (Phosphate glass-polymer emulsions", *Ceramic Transactions,* Volume 33, 1993). Organic-inorganic blends have also been formed by intercalation of polymers in the melt between mica sheets; Giannelis ("A New Strategy For Synthesizing Polymer-Ceramic Nanocomposites", *Journal of the Minerals, Metals and Materials Society,* Volume 44. Number 3, 1992). These processes have resulted in a class of materials called ceramers that possess properties of both inorganic glasses and organic polymers.

Organic-inorganic blends may also be produced by utilizing the sol-gel process. With this method, the inorganic phase is formed in-situ by hydrolysis and polycondensation of the alkylated metal aldoxides. Alkylated metal oxides are organic low molecular weight compounds soluble in organic solvents which precipitate as metal oxides upon condensation. Sol-gel ceramers in the past have involved the formation of transparent or translucent thin films where the organic and inorganic phases are co-mingled and then cured, as described by Iyoku et al, (The Preparation of New Poly(phenylsilsesquioxane)-Polyimide Hydrid Films by the Sol-Gel Process and Their Properties", *High Performance Polymers,* Volume 6, 1994), where they indicate the formation of small particles of silicone dispersed in a film.

In another case where inorganic-organic composites are formed, the functionality of the poly(dimethylsiloxane) chains of the polymer results in strong interactions between the two components, where the polymer constitutes the continuous phase, while the ceramic material serves as reinforcing particles. When the polymer is present in lower concentrations, it becomes dispersed in the continuous ceramic phase. Mark et al, ("Inorganic-Organic Composites Including Some Examples Involving Polyamides and Polyimides", *Macromolecular Symposium,* Volume 98, 1995), even cites cases where a bicontinuous system is formed.

Another method of generating organic-inorganic blended materials is by encapsulation. This technology is being used extensively in many industries and for a wide variety of materials. Microcapsules can have many different structures, but typically involve a core region surrounded by a shell. The geometry may be spherical or irregular, and contain a continuous core or small particles of core material surrounded by the shell. As a result of agglomeration, traditional methods of encapsulating metal oxide particles result in a multi-molecular/multi-nuclear core region surrounded by a coating. Macro Coated Particle (MCP) technology results in organic-inorganic particles in the ten to hundreds of micron range (FIG. 1). Molecular Level Coating (MLC) technology, as employed in the present invention (FIG. 2), utilizes microencapsulation technology in conjunction with sol-gel processing. The in-situ generation of the inorganic phase with MLC results in a polymer coated, molecular level, metal oxide particle in the angstrom size range.

Preparation of a ceramer by MLC results in the formation of the metal oxide as a discrete particle thinly coated with a polymer. MLC of a preceramic and a high performance polymer facilitates the design of systems that combine the thermal stability, high stiffness (modulus) or light reflective properties of a glass with the toughness and processability of a polymer. MLC further offers the advantage of metal oxide particles with less abrasive properties than uncoated metal oxides.

Titanium oxide, a commonly used whitener in pigments and coatings, is subject to weathering with long term exposure to sunlight. Exposure to ultraviolet light results in excitation of the electrons in the titanium compound which may return to the ground state by transferring free radicals to the surrounding materials. Absorption of these free radicals by the surrounding organic material leads to discoloration and degradation. In accordance with the present invention, degradation of titanium oxide is slowed by encapsulating the titanium oxide particles in a polymer that is nonreactive to free radical bombardment.

SUMMARY OF THE INVENTION

It an object of the present invention to provide a molecular level coated metal oxide particle that has less abrasive properties than uncoated metal oxide particles.

A further object of the present invention is to provide a metal oxide encapsulated with a polyimide that has synergistic property characteristics.

Another object of the present invention is to provide encapsulated titanium oxide particles to decrease the degradation and improve the weathering and colorfast property characteristics of the particles.

An additional object of the present invention is a process of encapsulation of metal oxide particles with a surrounding insulation of a polyimide to thereby insulate the metal oxide from free radical transfer and provide better weathering and good resistant color fast properties to the metal oxide.

A further object of the present invention is to provide an encapsulated titanium oxide for use in a protective urguent for human skin.

An additional object of the present invention is to provide coated metal oxide particles that hinder the loss of free radicals when exposed to ultraviolet light.

Another object of the present invention is a process of preparing molecular level coatings of metal oxide particles for use as ultraviolet and weather protectives in unguents for human skin, paper fillers, printing inks, fiber reinforced composites and textiles.

Another object of the present invention is a polymer encapsulated metal oxide matrix resin for manufacturing fiber reinforced composites wherein the metal oxide particles increase the modulus of the polymer in the composite.

The foregoing and additional objects are attained by employing, as the metal oxide coating, a polyimide having repeating units of:

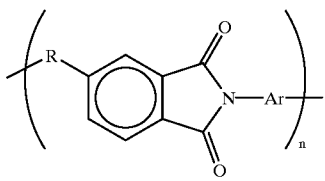

wherein Ar is a member selected from the group consisting of:

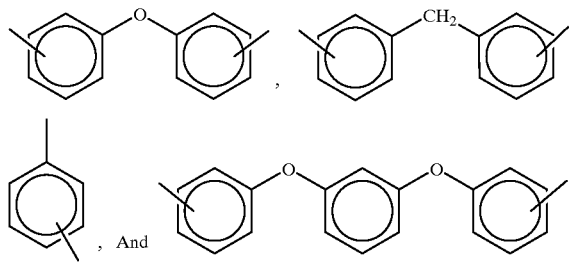

wherein the catenation is meta, meta; meta, para; or para, para;

wherein R is a member selected from the group consisting of:

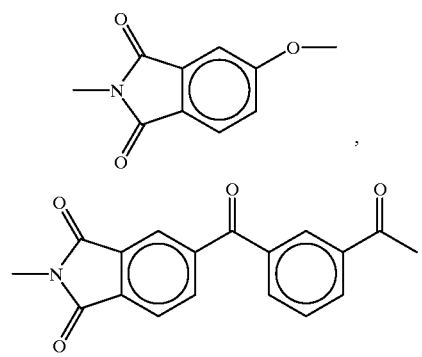

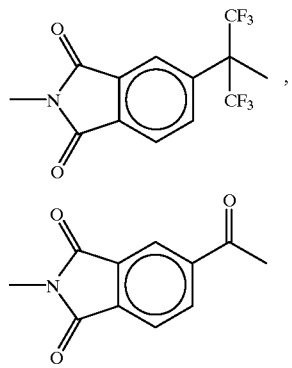

and, wherein n is an integer in the range of 10 to 10,000.

Polymer encapsulated metal oxide particles were prepared by combining a polyamide acid in a polar aprotic solvent with a metal alkoxide solution. The polymer was imidized and the metal oxide formed simultaneously in refluxing organic solvent. The resultant polymer-metal oxide is an intimately mixed commingled blend, possessing properties of both the polymer and preceramic metal oxide.

Polymers suitable for practice of the present invention are disclosed in the following U.S. Patents (incorporated herein by reference), U.S. Pat. No. 4,094,482 (LARC™ TPI); U.S. Pat. No. 4,603,061 (LARC™ 6F); U.S. Pat. No. 4,937,317 (LARC™ ITPI);, and U.S. Pat. No. 5,147,966 (LARC™ IA), and are commercially available from NASA licensees of these patents.

BRIEF DESCRIPTION OF THE DRAWINGS

A more complete appreciation of the invention and many of the attendant advantages thereof will be more readily apparent as the same becomes better understood in connection with the following drawings and specific examples wherein:

FIG. 1 is a schematic representation of a polymer coating of macro metal oxide particles;

FIG. 2 is a schematic representation of a polymer coating of a molecular level metal oxide particle;

FIG. 3 is a bar graph showing the improved flexural modulus of the polymer coated molecular level metal oxide particles over the unmodified polymer;

DETAILED DESCRIPTION

Figure 4:
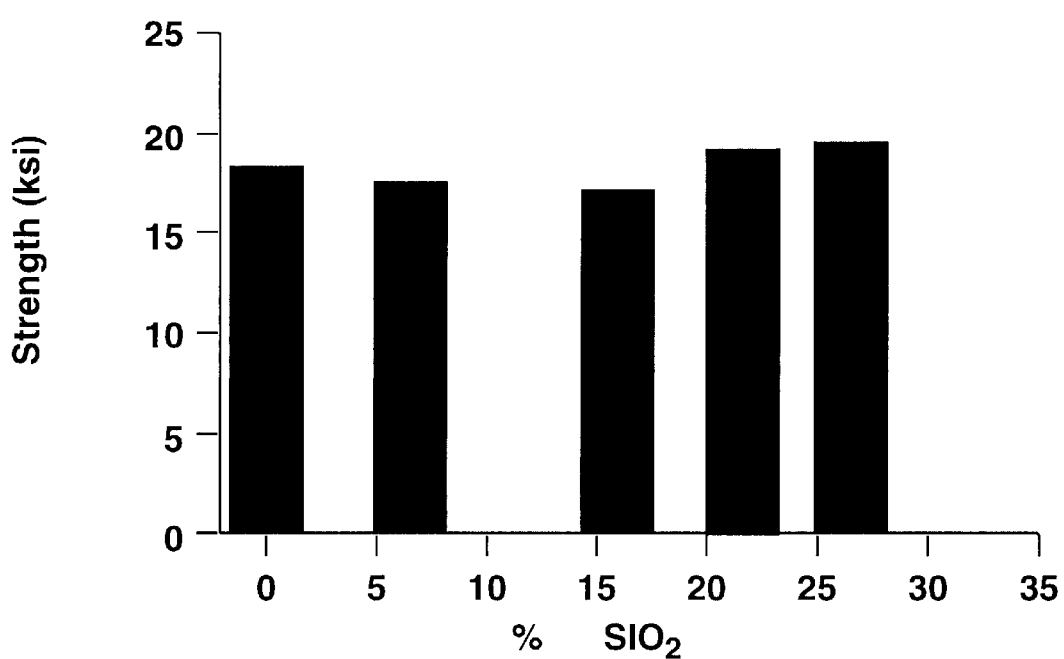
FIG. 4 is a bar graph showing the improved flexural strength of the polymer coated molecular level metal oxide particles over that of the unmodified polymer.

Referring to the drawings, FIG. 1 is a schematic representation of a macro coated particle, designated generally by reference numeral 10 is shown. Coated particle 10 consists of a multimolecular metal oxide particle 12 having a polymer coating 14 thereon. These coated particles are in the micron size range and are developed by Macro Coated Particle Technology (MCP).

FIG. 2 is a schematic representation of a molecular metal oxide coated particle, generally designated by reference numeral 20. Coated particle 20 consists of a single molecule of a metal oxide 22 having a polymer coating 24 thereon. This coated particle is in the angstrom size range and is developed by Molecular Level Coating Technology (MLC). The present invention is confined to Molecular Level Coating Technology (MLC) and the products produced thereby.

These encapsulated particles offer properties of the metal oxide and polymer which are not related simply to a rule of mixtures but appear to be synergistic in character. Encapsulation results in insulation of the surrounding medium from free radical transfer resulting in materials with better weathering and good resistant color fast systems.

The insulative coating serves as protection from the environment. Thus, in one application of the present invention, the metal oxide, such as $TiO_2$, is mixed with a cosmetic base to afford a resulting material having enhanced stability to ultraviolet light, to serve as a protective unguent for human skin. The photosensitive $TiO_2$ is isolated from the cosmetic binder thereby decreasing binder decomposition as a result of free radical transfer. This insulating effect also serves to protect the skin from negative physiological effects due to free radical attack that often results in adverse chemical reactions.

When employing the coated metal oxide particles of the present invention as a filler for paints and coatings, the insulative properties of the coated metal oxide particles are effective. The supporting medium of the coating and its surrounding environment, is protected by these insulative properties from free radical transfer as a result of ultraviolet exposure to thereby decrease chalking.

When employing the coated metal oxide particles of the present invention as a filler for papers, the encapsulated metal oxide serves as a whitener to the paper, while decreasing the yellowing normally caused by environmental exposure.

The coated metal oxide particles of the present invention are also useful as an additive to printing inks. In this environment, the high performance polymer provides lubrication to the pigments, resulting in a less chalky medium with decreased friction, while the metal oxide provides the desired pigmentation.

As will be further described hereinafter, when employing the polymer coated metal oxide particles of the present invention as a matrix resin for fiber reinforced composites, the metal oxide particles increase the flexural modulus of the polymer in the composite.

When employing the polymer coated metal oxide particles of the present invention as a filler for textiles, the metal oxide serves as a whitener and the insulative properties of the high performance polymer serves to protect the fiber from weathering.

DESCRIPTION OF THE PREFERRED EMBODIMENTS AND SPECIFIC EXAMPLES

In preparing the polyimide-titanium oxide blend, the polyamide acid form of LARC™ IA in N-methyl pyrrolidinone (NMP) and available from Imitech Corporation, was imidized by introducing it directly into a mixture of refluxing o-zylene and alkyl titanate, (both available from Aldrich Chemical Company). The water formed from ring closure during imidization facilitated the formation of the metal oxide. This results in the formation of the metal oxide as a discrete particle thinly coated with the polymer. The fine powder was recovered and dried under vacuum 12 hours at 200° C. All of the systems formed fine powders which dispersed well in lacquers, oil based coatings, and epoxy. In lieu of N-Methyl pyrrolidinone, gamma-butyrolactone, N,N-dimethylacetamide, 1,3-dimethyl-2-imidazolidinone, and others, may be utilized as the solvent in this process. Although the polyimides employed in the specific examples herein were from the soluble polyamide acid forms, soluble polyimides may also be used, in particular, LARC™ IA and LARC™ 6F.

Example I

Reaction Sequence for the Synthesis of a Polymer-metal Oxide Encapsulated Molecular Level Particle Into a resin kettle equipped with a mechanical stirrer, nitrogen inlet, moisture trap and reflux condenser was added 300 ml of o-xylene. The resin kettle was wrapped in glass wool and the solvent heated to reflux.

A 10 g sample of 10 weight percent solution of polymer in NMP was combined with 10 g of metal alkoxide and 10 g of water and allowed to stir until homogeneous. The resin mixture was added dropwise via an addition funnel into the refluxing o-xylene. The system was allowed to heat at approximately 140° C., with stirring overnight, the solids collected and dried under vacuum 12 hours at 200° C. Yield 11 grams of fine off-white powder. Examples of polymer oxides formed are summarized in Table I.

TABLE I

| Polymer | Titanium Oxide | Zirconium Oxide | Silica Oxide |
| --- | --- | --- | --- |
| LARC ™ IA | Off-white powder | Light orange powder | Light brown powder |
| LARC ™ TPI | Off-white powder | Light orange powder | Light brown powder |
| LARC ™ I-TPI | Off-white powder | Light orange powder | Light brown powder |
| LARC ™ 6-F | White powder | Light pink powder | Off-white powder |

Example II

The same as in Example I except gamma-butyrolactone was employed as the solvent in lieu of NMP.

Example III

The same as in Example I except, in lieu of NMP, the solvent employed is N,N-dimethylacetamide.

Example IV

The same as in Examples I except, in lieu of NMP, the solvent employed is 1,3-dimethyl-2-imidazolidinone.

Example V

Synthesis of a Polymer-titanium Oxide Blend

Into a 10 liter resin kettle equipped with a mechanical stirrer, nitrogen inlet, moisture trap and reflux condenser was placed 5,000 ml of o-xylene. The resin kettle was wrapped in glass wool and heated to reflux.

1330 ml of tetrakis(2-ethylhexyl)orthotitanate (alkyl titanate) was added to the hot o-xylene and allowed to heat 30 minutes at approximately 140° C.

LARC™ IA, 230 g of 30 weight percent in NMP at 3% stoichiometric offset endcapped with phthalic anhydride was diluted with 1300 g of distilled NMP. The resin mixture was added dropwise via an addition funnel into the refluxing o-xylene over a 2 hour period. The system was allowed to heat at approximately 140° C. with stirring for 48 hours. The light brown slurry was centrifuged and the solvent decanted off. The recovered off-white powder was washed in o-xylene, collected on medium porosity sintered glass, and dried 12 hours at 200° C. under vacuum. The yield was 63.7 g, 5% weight loss by thermogravimetric analysis at 324° C.

Example VI

The same as Example V except, in lieu of NMP, the solvent employed is gamma-butyrolactone.

Example VII

The same as Example V except, in lieu of NMP, the solvent employed is N,N-dimethylacetamide.

Example VIII

The same as Example V except, in lieu of NMP, the solvent employed is 1,3-dimethyl-2-imidazolidinone.

The molar ratios of metal oxide to polymer formed in Examples V to VIII are summarized in TABLE II below:

TABLE II

| LARC ™ IA Moles | Alkyl Titanate Moles | $H_2O$ Moles | Molar Ratio of Metal Oxide to Polymer |
|---|---|---|---|
| $3.2 \times 10^{-2}$ | $8.6 \times 10^{-2}$ | 2.68 | 2.7:1 |
| $9.5 \times 10^{-2}$ | .51 | | 5.4:1 |
| 0.15 | 2.3 | | 15:1 |

Example IX

Preparation of a Skin Unguent

A skin unguent was prepared by mixing one part, by weight, of the powder prepared in Example I to 1 to 10 parts, by weight, of mineral oil.

Example X

A skin unguent was prepared by mixing one part, by weight, of the powder prepared in Example I, with 1 to 10 parts by weight, of glycerin.

Example XI

A skin unguent was prepared by mixing one part, by weight, of the powder prepared in Example I, with an emulsion comprising 0.5 to 4 parts, by weight, of glycerin; 0.5 to 4 parts, by weight, of mineral oil; and 0.25 to 1 part, by weight, of water.

In each of Examples IX, X and XI, a resulting unguent having a color indicative of that of the polymer powder employed, was obtained that, when spread on the skin, left a protective coating.

The ratios of the ingredients in the skin unguent produced by Examples IX, X and XI are summarized in TABLE III below:

TABLE III

| MLC Powder (mg) | Mineral Oil (mg) | Glycerin (mg) | Water (mg) |
|---|---|---|---|
| 250 | 250 | | |
| 250 | 1250 | | |
| 250 | 2500 | | |
| 250 | | 250 | |
| 250 | | 1250 | |
| 250 | | 2500 | |
| 250 | 125 | 125 | 10 |
| 250 | 250 | 250 | 25 |
| 250 | 500 | 500 | 100 |
| 250 | 1000 | 1000 | 250 |

Example XII

Preparation of Filled Paints and Coatings

A 50 mg aliquot of the sample prepared in Example I was combined with 100 mg of binder. The binder was allowed to dry 24 hours and a light tan coating resulted. Table IV summarizes the binders employed in the preparation of the paints and coatings.

TABLE IV

| Binder (100 mg) | mg of encapsulated $TiO_2$ | Result |
|---|---|---|
| Tung Oil | 50 | Light Tan Coating/Paint |
| Clear Vinyl Lacquer | 50 | Light Tan Coating/Paint |
| Epoxy Resin | 50 | Light Tan Cured Epoxy |
| Rubber Cement | 50 | Light Tan Film Flexible |

The lacquer employed in the Example above was "SO SURE" lacquer, obtained from LHB Industries, Berkley, Mo.; the epoxy resin was "bis phenol A diglycidyl ether" with polymercapton hardener, and acquired from the Devcon Corporation; and the rubber cement was "Carter's Rubber Cement" (Carter's Ink Division) and acquired from Demmison Manufacturing Company.

Example XIII

Preparation of a Filled Paper 8 g of cellulose pulp was slurried with 1 g of the powder prepared in Example II. The water was extracted and the filled pulp was collected over a suction apparatus at approximately 15 psi and allowed to dry at ambient temperature.

Example XIV

A 5 g aliquot of the powder prepared in Example II was added to 50 g of printing ink ("Numbering Ink", acquired from Bates Manufacturing Company). The filled ink was used to print on paper and exhibited stability to UV light. Ratios, other than the 1:10 polymer to ink, employed in this specific example would be expected to also be operative to provide a UV light stable ink.

Example XV

Reaction Sequence for Preparation of a Polymer-silica Oxide Blend

Into a 20 liter resin kettle equipped with a mechanical stirrer, nitrogen inlet, moisture trap and reflux condenser, was placed 12,000 ml of o-xylene. The resin kettle was wrapped in glass wool and heated to reflux.

LARC™ IA (1455 g, 30 weight percent) in NMP, at 3% stoichiometric offset and endcapped with phthalic anhydride, was diluted to 15% solids with distilled NMP. An alkyl silicate, tetraethylorthosilicate (TEOS, 436 ml) and distilled water (436 ml) was added slowly to the resin mixture. The solution was stirred for 5 hours, then added dropwise via an addition funnel into the resin kettle of refluxing o-xylene over a 2 hour period. The system was allowed to heat at approximately 140° C. with stirring, for 16 hours. During the duration of heating, 780 ml of aqueous material was collected in the moisture trap. The light brown slurry was centrifuged and the solvent decanted off. The remaining light brown powder was collected over medium porosity sintered glass and dried 12 hours at 200° C. under vacuum. Test specimens yielded improved mechanical properties over the unmodified polymer and are presented in FIGS. 3 and 4. Examples of molar ratios of metal oxide to polymer are summarized in TABLE V below:

TABLE V

| LARC ™ IA Moles | Alkyl Silicate Moles | Alkyl Zirconate Moles | $H_2O$ Moles | Molar Ratio of Metal Oxide to Polymer |
|---|---|---|---|---|
| 0.92 | 5.4 | | 48 | 6:1 |
| 0.26 | 0.78 | | 6.9 | 3:1 |
| $5.3 \times 10^{-2}$ | | 0.11 | | 2:1 |
| $5.3 \times 10^{-2}$ | $1.5 \times 10^{-2}$ | $6.9 \times 10^{-2}$ | 0.14 | 1.5:1 |
| $5.3 \times 10^{-2}$ | $7.8 \times 10^{-2}$ | $3.8 \times 10^{-2}$ | 0.69 | 2:1 |

Example XVI

The powder obtained from Example XV was passed through a Brabender melt extruder heated to 315° C. at a volume rate of 0.0105 $cm^3$ $sec^{-1}$. Melt extrusion yielded polymer fiber or ribbon.

Example XVII

Fiber Reinforced Composite Panel

Figure 5:
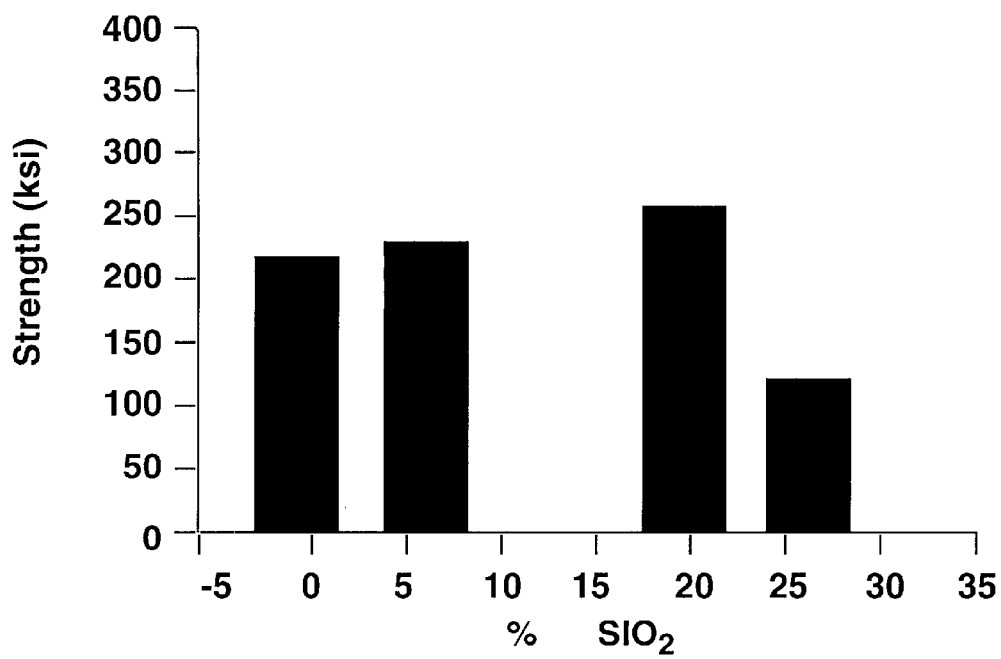
FIG. 5 is a bar graph showing the flexural strength of a composite specimen formed of metal oxide-polyimide prepared according to the present invention employed as a carbon fiber coating and molded into a composite panel; and, FIG. 6 is a bar graph showing the flexural modulus of the composite specimen formed of metal oxide-polyimide prepared according to the present invention employed as a carbon fiber coating and molded into a composite panel.
Figure 6:
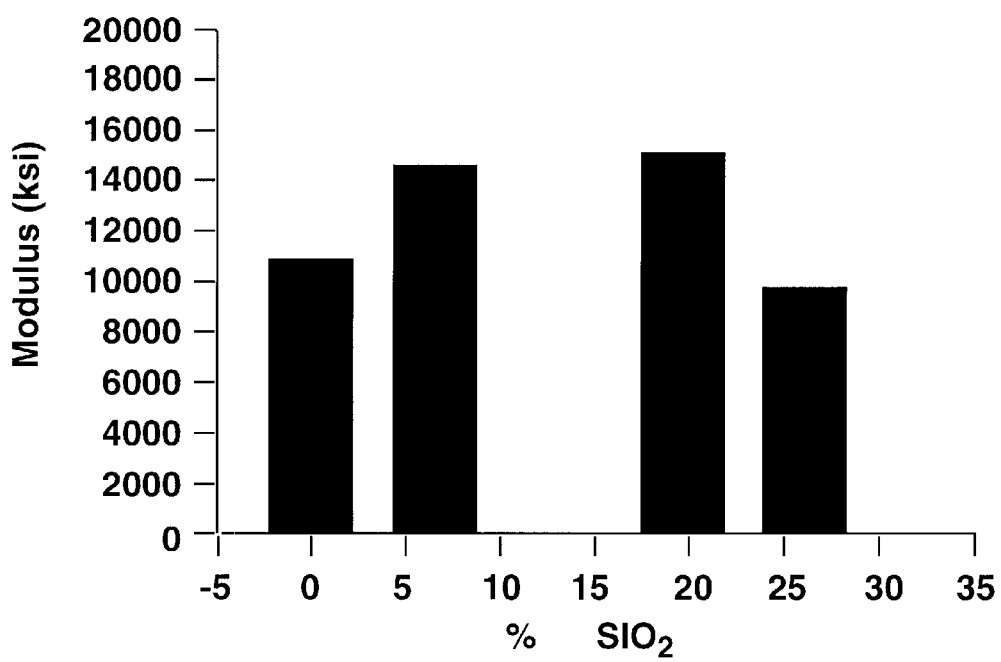

A powder coated towpreg was prepared by coating carbon fibers with the modified polymer prepared in Example XV. The powder coated towpreg was then wound around a frame, stacked in a mold and consolidated under 300 psi one hour at 350° C. The composite specimen was slowly cooled to room temperature prior to removal from the mold. Test panels yielded panels with the strength properties plotted in FIG. 5 and modulus properties as plotted in FIG. 6.

Example XVIII

Reaction Sequence for the Synthesis of a Polymer-metal Oxide/Metal Oxide Encapsulated Particle Into a resin kettle equipped with a mechanical stirrer, nitrogen inlet, moisture trap and reflux condenser was placed 300 ml of o-xylene. The resin kettle was wrapped in glass wool and the solvent heated to reflux.

A 10 g sample of 10 weight percent solution of polymer in NMP was combined with 1 g of alkyl silicate (TEOS) and 9 g of zirconium butoxide and allowed to stir until homogeneous. The resin mixture was added dropwise via an addition funnel into the refluxing o-xylene. The system was allowed to heat at approximately 140° C. with stirring overnight, the solids collected and dried under vacuum 12 hours at 200 ° C.

Example XIX

Synthesis of a Polymer-metal Oxide/Metal Oxide Encapsulated Particle

Into a resin kettle equipped with a mechanical stirrer, nitrogen inlet, moisture trap and reflux condenser, was placed 300 ml of o-xylene. The resin kettle was wrapped in glass wool and the solvent heated to reflux.

A 10 g sample of 10 weight percent solution of polymer in NMP was combined with 9 g of alkyl silicate (TEOS) and 1 g of zirconium butoxide and allowed to stir until homogeneous. The resin mixture was added dropwise via an addition funnel into the refluxing o-xylene. The system was allowed to heat with stirring overnight, the solids collected and dried under vacuum 12 hours at 200° C.

The foregoing specific examples are given to illustrate the principal of the invention and, as such, are to be considered as exemplary and not exhaustive. There are numerous modifications and variations of the present invention that will be readily apparent to those skilled in the art in the light of the above teachings.

For example, where specific quantities and ratios are employed it is to be understood that the invention is not so limited and that these specifics are to illustrate specific examples and reactions, and are not to serve as limitations on the invention. Other quantities and ratios that may be apparent to those skilled in the art, and within the scope of the appended claims, are intended to be included herein.

It is therefore to be understood that, within the scope of the appended claims, the invention may be practiced other than as specifically described herein.

What is claimed as new and desired to secured by Letters Patent of the United States is:

1. A process of making a polymer encapsulated metal oxide product wherein the individual molecules of the metal oxide are coated with the polymer comprising the steps of:

combining a polyamide acid in a polar aprotic solvent with a metal alkoxide solution, refluxing the resulting solution to simultaneously imidize the polymer and form the metal oxide to provide an intimately mixed commingled blend;

filtering the blend to recover the resulting solids; and drying the collected solids under vacuum to recover a powder having properties of both the polymer and preceramic metal oxide.

2. The process of claim 1 wherein the metal alkoxide solution is selected from the group of metal alkoxide solutions consisting of an alkyl titanate, an alkyl zircononate and an alkyl silicate.

3. The process of claim 1 wherein the polar aprotic solvent is selected from the group of aprotic solvents consisting of N-methyl pyrrolidinone (NMP), gamma-butyrolactone, N,N-dimethylacetamide, and 1,3-dimethyl-2-imidazolidinone.

4. The process of claim 1 wherein the step of refluxing the resultant solution includes providing a resin kettle equipped with a mechanical stirrer, nitrogen inlet, moisture trap and reflux condenser and containing a quantity of o-xylene reflux liquid.

5. The process of claim 1 wherein the polymer coating is a polyimide having repeating units of:

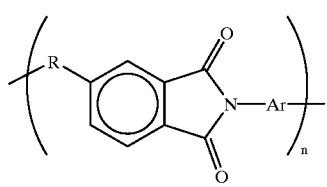
wherein Ar is an organic moiety selected from the group of organic moieties consisting of:
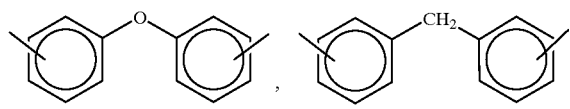
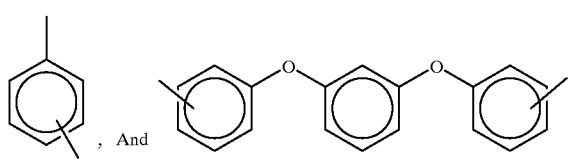
wherein the catenation is meta, meta; meta, para; or para, para;
wherein R is an organic moiety selected from the group of organic moieties consisting of:
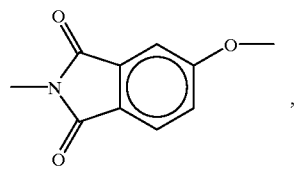
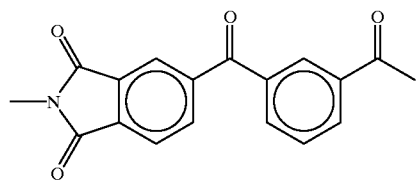
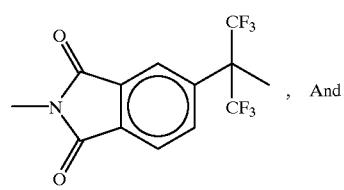
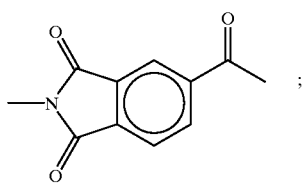
and, wherein n is an integer in the range of 10 to 10,000.
* * * * *